US007083916B2

(12) United States Patent
Lester et al.

(10) Patent No.: US 7,083,916 B2
(45) Date of Patent: Aug. 1, 2006

(54) DNA ENCODING INWARD RECTIFIER, G-PROTEIN ACTIVATED, MAMMALIAN, POTASSIUM KGA CHANNEL AND USES THEREOF

(75) Inventors: Henry A. Lester, South Pasadena, CA (US); Nathan Dascal, South Pasadena, CA (US); Nancy F. Lim, Pasadena, CA (US); Wolfgang Schreibmayer, South Pasadena, CA (US); Norman Davidson, Sierra Madre, CA (US)

(73) Assignee: California Institute of Technology, Pasadena, CA (US)

( * ) Notice: Subject to any disclaimer, the term of this patent is extended or adjusted under 35 U.S.C. 154(b) by 427 days.

(21) Appl. No.: 09/812,074

(22) Filed: Mar. 19, 2001

(65) Prior Publication Data

US 2002/0086298 A1    Jul. 4, 2002

Related U.S. Application Data

(63) Continuation of application No. 09/042,494, filed on Mar. 16, 1998, now Pat. No. 6,255,459, which is a continuation of application No. 08/066,371, filed on May 21, 1993, now Pat. No. 5,747,278.

(51) Int. Cl.
*C12Q 1/68* (2006.01)
(52) U.S. Cl. .................... 435/6; 435/7.2; 435/69.1; 536/23.5
(58) Field of Classification Search .............. 435/6
See application file for complete search history.

(56) References Cited

U.S. PATENT DOCUMENTS

| 5,492,825 A | * | 2/1996 | Jan et al. ............... 435/352 |
| 5,670,335 A | * | 9/1997 | Jan et al. ............... 435/29 |
| 5,728,535 A | * | 3/1998 | Lester et al. ............ 435/6 |
| 5,734,021 A | * | 3/1998 | Lester et al. ............ 530/350 |
| 5,744,324 A | * | 4/1998 | Lester et al. ............ 435/69.1 |
| 5,744,594 A |   | 4/1998 | Adelman et al. |

OTHER PUBLICATIONS

Adams, M.D. et al., "Sequence identification of 2,375 human brain genes", Nature 355:632-634 (1992).
Adams, M.D. et al., Genbank Acc. No. M78731 (database record) (1992).
Ho, K. et al., "Cloning and expression of an inwardly rectifying ATP-regulated Potassium channels", Nature 362:31-38 (1993).
Kubo, Y. et al., "Primary structure and functional expression of a mouse inward rectified potassium channel", Nature 362:127-133 (1993).
Karschin, A. et al., "Heterologously expressed serotonin 1A receptors couple to muscarinic K+ channels in heart", Proc. Natl. Acad. Sci. USA 88:5694-5698 (1991).
Dascal, N. et al., "Atrial G protein-activated K+ channel: expression cloning and molecular properties", Proc. Natl. Acad. Sci. USA 90:10235-10239 (1993).
Dascal, N. et al., "Expression of atrial G-protein-activated potassium channel in *Xenopus oocytes*", Proc. Natl. Acad. Sci. USA 90:6596-6600 (1993).
Hemmings, B.A. et al., "α- and β-Forms of the 65-kDa subunit of protein phosphatase 2A have a similar 39 amino acid repeating structure", Biochemistry 29:3166-3173 (1990).
Sambrook, et al., "Chap. 11 Synthetic Oligonucleotide Probes", Molecular Cloning 2nd ed. New York, Cold Spring Harbor (1989).
Lesage, F. et al., "Cloning provides evidence for a family of inward rectifier and G-protein coupled K+ channels in the brain", FEBS Letters 353:37-42 (1994).
Sakmann, B. et al., "Acetylcholine activation of single muscarinic K+ channels in isolated pacemaker cells of the mammalian heart", Nature 303:250-253 (1983).

(Continued)

*Primary Examiner*—Michael Pak
(74) *Attorney, Agent, or Firm*—Richard F. Trecartin; Jeffery P. Bernhardt; Dorsey & Whitney LLP

(57) ABSTRACT

This invention provides isolated nucleic acid molecules which encode inward rectifier, G-protein activated, mammalian, potassium KGA channel. This invention also provides a nucleic acid molecule of at least 15 nucleotides capable of specifically hybridizing with the above nucleic acid molecule. This invention further provides a vector comprising the isolated nucleic acid molecules which encode inward rectifier, G-protein activated, mammalian, potassium KGA channel. This invention provides a host vector system for the production of a polypeptide having the biological activity of KGA channel which comprises the above vector in a suitable host. This invention also provides a method for isolating from a sample a nucleic acid molecule encoding an inward rectifier, G-protein activated, potassium channel in a sample which comprises: (a) isolating the nucleic acids from the sample; (b) contacting the isolated nucleic acids with the molecule of at least 15 nucleotides capable of specifically hybridizing with the above nucleic acid molecule which encode inward rectifier, G-protein activated, mammalian, potassium KGA channel under the conditions permitting complex formation between the nucleic acid molecule encoding an inward rectifier, G-protein activated, potassium channel and the nucleic acid molecule of at least 15 nucleotides capable of specifically hybridizing with the above nucleic acid molecule which encode inward rectifier, G-protein activated, mammalian, potassium KGA channel; (c) isolating the complex formed; and (d) separating the nucleic acid molecule encoding an inward rectifier, G-protein activated, potassium channel from the complex, thereby isolating the nucleic acid molecule encoding an inward rectifier, G-protein activated, potassium channel.

2 Claims, 9 Drawing Sheets

OTHER PUBLICATIONS

Yatani, Y. et al., "Direct activation of mammaliam atrial muscarinc potassium channels by GTP regulatory protein $G_k$", Science 235:207-211 (1987).

Kubo, Y. et al., "Primary structure and functional expression of a rat G-protein-coupled mascarinic potassium channel", Nature 364:802-806 (1993).

Adams, R.L.P. et al., "The biochemistry of the nucleic acids", 9th ed. London: Chapman and Hall, p. 124 (1981).

Brown, A.M., "Regulation of heartbeat by G protein-coupled ion channels", Am. J. Physiol., 259(6):H1621-H1628 (1990).

Kirsch, G.E. et al., "Trpsin activation of atrial muscarinic K+ channels". Am. J. Physiol., 26(1):H334-H338 (1989).

Aldrich, R., "Potassium channels: Advent of a new family", Nature 362:107-108 (1993).

* cited by examiner

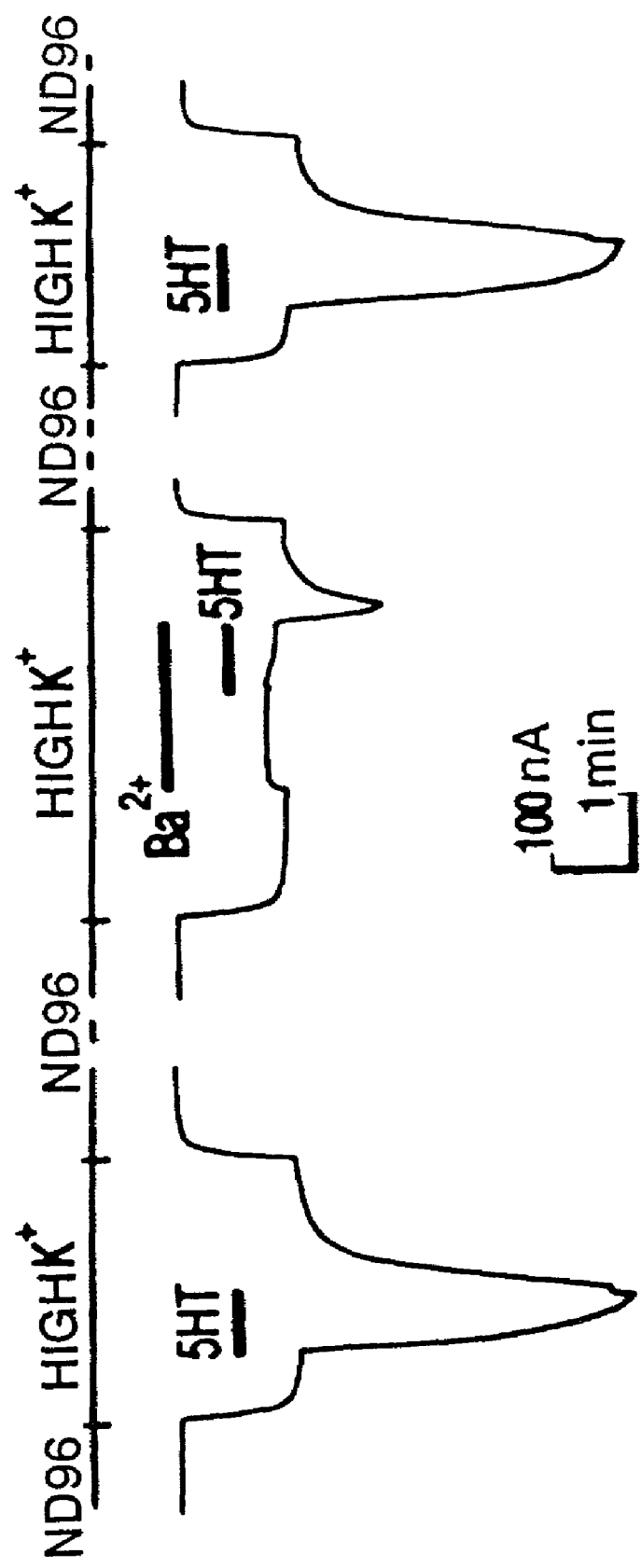

FIGURE 5

```
  1 GGCA CGA GAA TCT GGA TCT CCC CTC CGT ATT ATG TCT GCA CTC CGA   46
  1                                              M   S   A   L   R    5

47 AGG AAA TTT GGG GAC GAT TAC CAG GTA GTG ACC ACT TCG TCC AGC   91
  6  R   K   F   G   D   D   Y   Q   V   V   T   T   S   S   S    20

92 GGT TCG GGC TTG CAG CCC CAG GGG CCA GGA CAG GGC CCA CAG CAG  136
 21  G   S   G   L   Q   P   Q   G   P   G   Q   G   P   Q   Q    35

137 CAG CTT GTA CCC AAG AAG AAA CGG CAG CGG TTC GTG GAC AAG AAC  181
 36  Q   L   V   P   K   K   K   R   Q   R   F   V   D   K   N    50

182 GGT CGG TGC AAT GTG CAG CAC GGC AAC CTG GGC AGC GAG ACC AGT  226
 51  G   R   C   N   V   Q   H   G   N   L   G   S   E   T   S    65

227 CGC TAC CTT TCC GAC CTC TTC ACT ACC CTG GTG GAT CTC AAG TGG  271
 66  R   Y   L   S   D   L   F   T   T   L   V   D   L   K   W    80

272 CGT TGG AAC CTC TTT ATC TTC ATC CTC ACC TAC ACC GTG GCC TGG  316
 81  R   W   N   L   F   I   F   I   L   T   Y   T   V   A   W    95

317 CTC TTC ATG GCG TCC ATG TGG TGG GTG ATC GCT TAT ACC CGG GGC  361
 96  L   F   M   A   S   M   W   W   V   I   A   Y   T   R   G   110

362 GAC CTG AAC AAA GCC CAT GTC GGC AAC TAC ACT CCC TGT GTG GCC  406
111  D   L   N   K   A   H   V   G   N   Y   T   P   C   V   A   125

407 AAT GTC TAT AAC TTC CCC TCT GCC TTC CTT TTC TTC ATC GAG ACC  451
126  N   V   Y   N   F   P   S   A   F   L   F   F   I   E   T   140

452 GAG GCC ACC ATC GGC TAT GGC TAC CGC TAC ATC ACC GAC AAG TGC  496
141  E   A   T   I   G   Y   G   Y   R   Y   I   T   D   K   C   155

497 CCC GAG GGC ATC ATC CTT TTC CTT TTC CAG TCC ATC CTT GGC TCC  541
156  P   E   G   I   I   L   F   L   F   Q   S   I   L   G   S   170

542 ATC GTG GAC GCT TTC CTC ATC GGC TGC ATG TTC ATC AAG ATG TCC  586
171  I   V   D   A   F   L   I   G   C   M   F   I   K   M   S   185

587 CAG CCC AAA AAG CGC GCC GAG ACC CTC ATG TTT AGC GAG CAT GCG  631
186  Q   P   K   K   R   A   E   T   L   M   F   S   E   H   A   200

632 GTT ATT TCC ATG AGG GAC GGA AAA CTC ACT CTC ATG TTC CGG GTG  676
201  V   I   S   M   R   D   G   K   L   T   L   M   F   R   V   215

677 GGC AAC CTG CGC AAC AGC CAC ATG GTC TCC GCG CAG ATC CGC TGC  721
216  G   N   L   R   N   S   H   M   V   S   A   Q   I   R   C   230

722 AAG CTG CTC AAA TCT CGG CAG ACA CCT GAG GGT GAG TTT CTA CCC  766
231  K   L   L   K   S   R   Q   T   P   E   G   E   F   L   P   245

767 CTT GAC CAA CTT GAA CTG GAT GTA GGT TTT AGT ACA GGG GCA GAT  811
246  L   D   Q   L   E   L   D   V   G   F   S   T   G   A   D   260

812 CAA CTT TTT CTT GTG TCC CCT CTC ACC ATT TGC CAC GTG ATC GAT  856
261  Q   L   F   L   V   S   P   L   T   I   C   H   V   I   D   275

857 GCC AAA AGC CCC TTT TAT GAC CTA TCC CAG CGA AGC ATG CAA ACT  901
276  A   K   S   P   F   Y   D   L   S   Q   R   S   M   Q   T   290
```

FIGURE 5(CONT.)

```
 902  GAA CAG TTC GAG GTG GTC GTC ATC CTG GAA GGC ATC GTG GAA ACC   946
 291   E   Q   F   E   V   V   V   I   L   E   G   I   V   E   T   305

947  ACA GGG ATG ACT TGT CAA GCT CGA ACA TCA TAC ACC GAA GAT GAA   991
 306   T   G   M   T   C   Q   A   R   T   S   Y   T   E   D   E   320

992  GTT CTT TGG GGT CAT CGT TTT TTC CCT GTA ATT TCT TTA GAA GAA  1036
 321   V   L   W   G   H   R   F   F   P   V   I   S   L   E   E   335

1037  GGA TTC TTT AAA GTC GAT TAC TCC CAG TTC CAT GCA ACC TTT GAA  1081
 336   G   F   F   K   V   D   Y   S   Q   F   H   A   T   F   E   350

1082  GTC CCC ACC CCT CCG TAC AGT GTG AAA GAG CAG GAA GAA ATG CTT  1126
 351   V   P   T   P   P   Y   S   V   K   E   Q   E   E   M   L   365

1127  CTC ATG TCT TCC CCT TTA ATA GCA CCA GCC ATA ACC AAC AGC AAA  1171
 366   L   M   S   S   P   L   I   A   P   A   I   T   N   S   K   380

1172  GAA AGA CAC AAT TCT GTG GAG TGC TTA GAT GGA CTA GAT GAC ATT  1216
 381   E   R   H   N   S   V   E   C   L   D   G   L   D   D   I   395

1217  AGC ACA AAA CTT CCA TCG AAG CTG CAG AAA ATT ACG GGA AGA GAA  1261
 396   S   T   K   L   P   S   K   L   Q   K   I   T   G   R   E   410

1262  GAC TTT CCC AAA AAA CTC CTG AGG ATG AGT TCT ACA ACT TCA GAA  1306
 411   D   F   P   K   K   L   L   R   M   S   S   T   T   S   E   425

1307  AAA GCC TAT AGT TTG GGT GAT TTG CCC ATG AAA CTC CAA CGA ATA  1351
 426   K   A   Y   S   L   G   D   L   P   M   K   L   Q   R   I   440

1352  AGT TCG GTT CCT GGC AAC TCT GAA GAA AAA CTG GTA TCT AAA ACC  1396
 441   S   S   V   P   G   N   S   E   E   K   L   V   S   K   T   455

1397  ACC AAG ATG TTA TCA GAT CCC ATG AGC CAG TCT GTG GCC GAT TTG  1441
 456   T   K   M   L   S   D   P   M   S   Q   S   V   A   D   L   470

1442  CCA CCG AAG CTT CAA AAG ATG GCT GGA GGA CCT ACC AGG ATG GAA  1486
 471   P   P   K   L   Q   K   M   A   G   G   P   T   R   M   E   485

1487  GGG AAT CTT CCA GCC AAA CTA AGA AAA ATG AAC TCT GAC CGC TTC  1531
 486   G   N   L   P   A   K   L   R   K   M   N   S   D   R   F   500

1532  ACA TAG CAA AAC ACC CCA TTA GGC ATT ATT TCA TGT TTT GAT TTA  1576
 501   T   *                                                        515

1577  GTT TTA GTC CAA TAT TTG GCT GAT AAG ATA ATC CTC CCC GGG AAA  1621

1622  TCT GAG AGG TCT ATC CCA GTC TGG CAA ATT CAT CAG AGG ACT CTT  1666

1667  CAT TGA AGT GTT GTT ACT GTG TTG AAC ATG AGT TAC AAA GGG AGG  1711

1712  ACA TCA TAA GAA AGC TAA TAG TTG GCA TGT ATT ATC ACA TCA AGC  1756

1757  ATG CAA TAA TGT GCA AAT TTT GCA TTT AGT TTT CTG GCA TGA TTT  1801

1802  ATA TAT GGC ATA TTT ATA TTG AAT ATT CTG GAA AAA TAT ATA AAT  1846

1847  ATA TAT TTG AAG TGG AGA TAT TCT CCC CAT AAT TTC TAA TAT ATG  1891

1892  TAT TAA GCC AAA CAT GAG TGG ATA GCT TTC AGG GCA CTA AAA TAA  1936

1937  TAT ACA TGC ATA CAT ACA TAC ATG CAT ATG CAC AGA CAC ATA CAC  1981
```

FIGURE 5 (CONT.)

```
1982  ACA CAT ACT CAT ATA TAT AAA ACA TAC CCA TAC AAA CAT ATA TAT    2026
2027  CTA ATA AAA ATT GTG ATG TTT TGT TCA AAA AAA AAA AAA AA         2070
```

DNA ENCODING INWARD RECTIFIER, G-PROTEIN ACTIVATED, MAMMALIAN, POTASSIUM KGA CHANNEL AND USES THEREOF

This is a continuation application of Ser. No. 09/042,494, filed on Mar. 16, 1998, now U.S. Pat. No. 6,255,459 which is a continuation of Ser. No. 08/066,371, filed May 21, 1993, now U.S. Pat. No. 5,747,278 issued May 5, 1998.

The invention disclosed herein was made with U.S. Government support under USPHS grants GM29836 and MH49176. Accordingly, the the U.S. government has certain rights in this invention.

BACKGROUND OF THE INVENTION

Throughout this application various publications are referenced by their reference number within parentheses. Full citations for these publications may be found at the end of the specification immediately preceding the sequence listing. The disclosures of these publications in their entireties are hereby incorporated by reference into this application in order to more fully describe the state of the art to which this invention pertains.

Parasympathetic regulation of the rate of heart contraction is exerted through the release of acetylcholine (ACh), which opens a $K^+$ channel in the atrium and thus slows the rate of depolarization that leads to initiation of the action potential (1,2). The coupling between binding of ACh to a muscarinic receptor and opening of the $K^+$ channel occurs via a pertussis toxin (PTX)-sensitive heterotrimeric G-protein, $G_k$ (3–5), probably belonging to the $G_i$ family (6,7). Activation of this G-protein-activated $K^+$ channel by $G_k$ does not require cytoplasmic intermediates (reviewed in refs. 8,9). However, a long-standing controversy exists as to which G-protein subunit couples to the KG channel. Purified βγ subunit complex (10,11) and α subunits of $G_i$ family (6,7,12) activate the KG channel in cell free, inside-out patches of atrial myocytes. Activation by the α subunits occurs at lower concentrations than that by βγ, but seems to be less efficient (13); the relative physiological importance of each pathway, as well as of possible involvement of the arachidonic acid pathway (14), is unclear.

A channel similar or identical to the ACh-operated KG can be activated in the atrium by adenosine (15), ATP (16), and epinephrine (17), probably also via a G-protein pathway. Furthermore, in nerve cells various 7-helix receptors such as serotonin 5HT1A, δ-opioid, $GABA_B$, somatostatin, etc., couple to similar $K^+$ channels, probably through direct activation by G-proteins (18–22). The similarity of the channels and of the signaling pathways in atrium and some nerve cell preparations was strengthened by the demonstration of the coupling of a neuronal 5HT1A receptor (5HT1A-R), transiently expressed in atrial myocytes, to the atrial KG (23).

By electrophysiological and pharmacological criteria, the atrial KGA channel belongs to a family of inward rectifiers that conduct $K^+$ much better in the inward than the outward direction, are blocked by extracellular $Na^+$, $Cs^+$ and $Ba^{2+}$, and are believed to possess a single-file pore with several permeant and blocking ion binding sites (24). Many inward rectifiers are not activated by transmitters or voltage but seem to be constitutively active. Inward rectification of the atrial KGA channel is due to block of $K^+$ efflux by intracellular $Mg^2$ (25), but for some channels of this family inward rectification may not depend on $Mg^{2+}$ block (26,27). The molecular structures of atrial and neuronal KGs are unknown. Inwardly rectifying $K^+$ channels structurally similar to voltage-activated $K^+$ channels have been cloned from plant cells (28,29). Recently, the primary structures of two mammalian inward rectifier channels have been elucidated by molecular cloning of their cDNAs via expression in Xenopus oocytes: an ATP-regulated $K^+$ channel from kidney, ROMK1 (30), and an inward rectifier from a macrophage cell line, IRK1 (31). Both appear to belong to a new superfamily of $K^+$ channels, with only two transmembrane domains per subunit and a pore region homologous to that of $K^+$, $Ca^{2+}$ and $Na^+$ voltage-dependent channels (see ref. 32). It has been hypothesized that the structure of G-protein activated inward rectifying $K^+$ channels should be similar to that of ROMK1 and IRK1 (31). Cloning of the atrial KGA channel and its expression in a heterologous system would be of importance not only for testing this hypothesis, but also because it will allow an as yet unexplored molecular approach to investigation of the mechanisms of direct G-protein-ion channel coupling. As a first step to cloning of the atrial KGA channel we have expressed it in Xenopus oocyte injected with atrial RNA and characterized the macroscopic current properties, including a preliminary characterization of G-protein coupling. We cloned the atrial KGA from a cDNA library derived from mRNA extracted from the heart of a 19 day old rat.

SUMMARY OF THE INVENTION

This invention provides isolated nucleic acid molecules which encode inward rectifier, G-protein activated, mammalian, potassium KGA channel.

This invention also provides a nucleic acid molecule of at least 15 nucleotides capable of specifically hybridizing with the above nucleic acid molecule.

This invention further provides a vector comprising the isolated nucleic acid molecules encoding an inward rectifier, G-protein activated, mammalian, potassium KGA channel.

This invention provides a host vector system for the production of a polypeptide having the biological activity of KGA channel which comprises the above vector in a suitable host.

This invention also provides a method for isolating from a sample a nucleic acid molecule encoding an inward rectifier, G-protein activated, potassium channel in a sample which comprises: (a) isolating the nucleic acids from the sample; (b) contacting the isolated nucleic acids with the molecule of at least 15 nucleotides capable of specifically hybridizing with the above nucleic acid molecule which encode inward rectifier, G-protein activated, mammalian, potassium KGA channel under the conditions permitting complex formation between the nucleic acid molecule encoding an inward rectifier, G-protein activated, potassium channel and the nucleic acid molecule of at least 15 nucleotides capable of specifically hybridizing with the above nucleic acid molecule which encode inward rectifier, G-protein activated, mammalian, potassium KGA channel; (c) isolating the complex formed; and (d) separating the nucleic acid molecule encoding an inward rectifier, G-protein activated, potassium channel from the complex, thereby isolating the nucleic acid molecule encoding an inward rectifier, G-protein activated, potassium channel.

BRIEF DESCRIPTION OF FIGURES

FIG 5. Nucleotide and deduced amino acid sequence encoding the inward rectifier, G-protein associated, mammalian, potassium KGA channel (SEQ ID NOS:1–2). Numbers in the right had margin correlate to nucleotide position and numbers below the amino acid sequence correlate with amino acid position.

DETAILED DESCRIPTION OF THE INVENTION

Figure 1A:
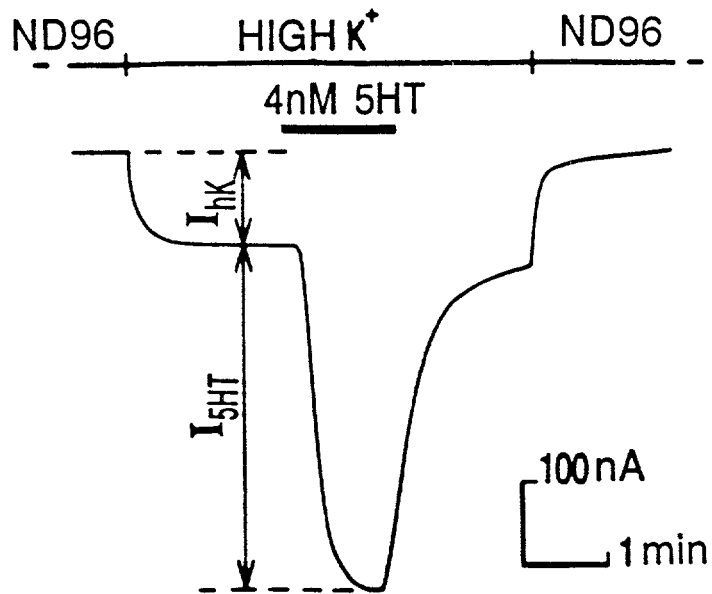
FIG. 1. Inward currents evoked by high $K^+$, 5HT and ACh in RNA-injected oocytes. (A) $I_{hk}$ and $I_{5HT}$ in an oocyte injected with atrial RNA+5HT1A-R RNA. Holding potential in this and all following Figures was −80 mV. (B) Inward currents evoked by ACh (AcCHo) and 5HT in a single oocyte in hK solution. (C) The dependence of $I_{5HT}$ amplitude on 5HT concentration in oocytes of one frog. In each oocyte, the response to one 5HT concentration was tested. Data represent mean±SEM in 4–6 cells at each concentration.

This invention provides isolated nucleic acid molecules which encode inward rectifier, G-protein activated, mammalian, potassium KGA channel. As used herein, the term inward rectifier, G-protein activated, mammalian, potassium KGA channel encompasses any amino acid sequence, polypeptide or protein having biological activities provided by the inward rectifier, G-protein activated, mammalian, potassium KGA channel. Furthermore the G-protein activation can be either directly or indirectly, and involve one or more G-proteins.

In one embodiment of this invention, the isolated nucleic acid molecules described hereinabove are DNA. In other embodiments of this invention, the isolated nucleic acid molecules described hereinabove are cDNA, genomic DNA or RNA. In the preferred embodiment of this invention, the isolated nucleic acid molecule is a cDNA as shown in sequence ID number 43717.APP.

This invention also encompasses DNAs and cDNAs which encode amino acid sequences which differ from those of inward rectifier, G-protein activated, mammalian, potassium KGA channel, but which should not produce functional changes in the KGA channel. This invention also encompasses nucleic acid molecules of at least 15 nucleotides capable of specifically hybridizing with the nucleic acid molecule which encode inward rectifier, G-protein activated, mammalian, potassium KGA channel. Hybridization methods are well known to those of skill in the art.

The DNA molecules of the subject invention also include DNA molecules coding for polypeptide analog, fragments or derivatives of substantially similar polypeptides which differ for naturally-occurring forms in terms of the identity of location of one or more amino acid residues (deletion analogs containing less than all of the residues specified for the protein, substitution analogs wherein one or more residues are replaced by other residues and addition analog wherein one or more amino acid residues is added to a terminal or medial portion of the polypeptides) and which share some or all properties of naturally-occurring forms. These sequences include: the incorporation of codons preferred for expressions by selected non-mammalian host; the provision of sites for cleavage by restriction endonuclease enzymes; the addition of promoters operatively linked to enhance RNA transcription; and the provision of additional initial, terminal or intermediate DNA sequences that facilitate construction of readily expressed vectors.

The nucleic acid molecule described and claimed herein is useful for the information which it provides concerning the amino acid sequence of the polypeptide and as products for the large scale synthesis of the polypeptide by a variety of recombinant techniques. The nucleic acid molecule is useful for generating new cloning and expression vectors, transformed and transfected procaryotic and eucaryotic host cells, and new and useful methods for cultured growth of such host cells capable of expressing the inward rectifier, G-protein activated, mammalian, KGA potassium channel and related polypeptides with biological activity of the KGA channel. Capable hosts for such host vector systems may include but are not limited to a bacterial cell, an insect cell, a mammalian cell, and a *Xenopus* oocyte.

The isolated RNA molecule described and claimed herein is useful for the information it provides concerning the amino acid sequence of the polypeptide and as a product for synthesis of the polypeptide by injecting the RNA molecules into *Xenopus* oocytes and culturing the oocytes under conditions that are well known to an ordinary artisan.

Moreover, the isolated nucleic acid molecules are useful for the development of probes to screen for and isolate related molecules from nucleic acid libraries other tissues, or organisms.

Inward rectifier, G-protein activated, mammalian, potassium KGA channel may be produced by a variety of vertebrate animals. In an embodiment, a rat inward rectifier, G-protein activated, mammalian, potassium KGA channel is isolated. A sequence of the DNA of rat inward rectifier, G-protein activated, mammalian, potassium KGA channel is shown in FIG. 5.

The resulting plasmid, pBSIIKS(−)KGA, encoding the rat inward rectifier, G-protein activated, mammalian, potassium KGA channel was deposited on May 17, 1993 with the American Type Culture Collection (ATCC), 12301 Parklawn Drive, Rockville, Md. 20852, U.S.A., under the provisions of the Budapest Treaty for the International Recognition of the Deposition of Microorganism for the Purposes of Patent Procedure. Plasmid, pBSIIKS(−)KGA, was accorded ATCC accession number 75469.

Throughout this application, references to specific nucleotides are to nucleotides present on the coding strand of the nucleic acid. The following standard abbreviations are used throughout he specification to indicate specific nucleotides:

C=cytosine
T=thymidine
A=adenosine
G=guanosine

For the purpose of illustration only, applicants used a cDNA plasmid library derived from 19-day-old rat atrial mRNA. The DNA was synthesized from the mRNA by reverse transcriptase using a poly(dt) primer with a XhoI overhang and was methylated. Adapters with EcoRI sites were ligated to both ends and the cDNA was digested with XhoI. It was ligated into XhoI–EcoRI-digested pBluescriptII KS(−). The library was linearized and amplified by polymerase chain reaction of the cDNA using primers that were complementary to sequences flanking the cDNA insert. cRNA was synthesized in vitro from the T7 promoter using T7 RNA polymerase. The cRNA was microinjected into *Xenopus laevis* oocytes and electrophysiological recordings under conditions described in Experimental Materials and Methods determined indentification of a inward rectifier, G-protein activated, mammalian, potassium KGA channel. Fewer and fewer cDNA clones from the library were used after identification of the KGA channel until the cDNA of the inward rectifier, G-protein activated, mammalian, potassium KGA channel was isolated.

This invention provides a nucleic acid probe comprising a nucleic acid molecule of at least 15 nucleotides capable of specifically hybridizing with a sequence included within the sequence of a nucleic acid molecule encoding an inward rectifier, G-protein activated, mammalian, potassium KGA channel. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skill in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes inward rectifier, G-protein activated, mammalian potassium KGA channel into suitable vectors, such as plasmids, bacteriophages, or retroviral vectors followed by transforming into suitable host cells and harvesting of the DNA probes, using methods well known in the art. Alternatively, probes may be generated chemically from DNA synthesizers.

The probes are useful for 'in situ' hybridization to locate tissues which express this gene, or for other hybridization assays for the presence of this gene or its in RNA in various biological tissues.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide having the biological activity of inward rectifier, G-protein activated, mammalian potassium KGA channel.

This invention further provides an isolated DNA or cDNA molecule described hereinabove wherein the host cell is selected from the group consisting of bacterial cells such as *E. coli*), yeast cells, fungal cells, insect cells and animal cells. Suitable animal cells include, but are not limited to Cos cells, HeLa cells, L(tk−), and various primary mammalian cells.

This invention provides a method for isolating from a sample a nucleic acid molecule encoding an inward rectifier, G-protein activated, potassium channel using the probe generated from the rat inward rectifier, G-protein activated, mammalian, potassium KGA channel gene. For the human, inward rectifier, G-protein activated, mammalian, potassium KGA channel, it is conceivable that the degree of homology between rat and human could be considerable. Homology studies of the inward rectifier, G-protein activated, mammalian, potassium KGA channel using Genetics Computer Group Sequence Analysis Software, Version 7.2, revealed 55% identity with Human clone HHCMD37 (Genbank Accession #M78731). Human heart cDNA library and human genomic library may be used for such screening. Duplicate filters of human libraries may be screened with radio labelled probe derived from the rat inward rectifier, G-protein activated, mammalian, potassium KGA channel DNA molecule. The filters containing the human libraries will be hybridized with the probe at low stringency (Sambrook, et al 1989) and positive clones identified.

This invention provides a method to identify and purify inward rectifier, G-protein activated, potassium channels. A sample of nucleic acid molecules can be screened for nucleic acid molecules capable of supporting complex formations with an inward rectifier, G-protein activated, mammalian, KGA potassium channels nucleic acid molecule of at least 15 nucleotides under conditions well known in the art that cause complex formation between nucleic acids molecules. "Sample" as used herein includes but is not limited to genomic libraries, cDNA libraries, nucleic acid molecule extracts from tissue, or nucleic acid molecule extracts from cell culture. Conditions that pertain to complex formation between nucleic acids are well understand by an ordinary skilled artisan and include but are not limited to suboptimal temperature, ionic concentration, and size of the nucleic acid molecule. After complex formation between the nucleic acid molecule encoding the inward rectifier, G-protein activated, mammalian, KGA potassium channel and another nucleic acid, the other nucleic acid molecule can be isolated by methods known in the art.

This invention provides a method for isolating from a sample a nucleic acid molecule encoding an inward rectifier, G-protein activated, potassium channel in a sample which comprises: (a) isolating the nucleic acids from the sample; (b) contacting the isolated nucleic acids with the nucleic acid molecule of at least 15 nucleotides capable of specifically hybridizing with the nucleic acid molecule of an isolated nucleic acid molecule encoding an inward rectifier, G-protein activated, mammalian, potassium KGA channel under the conditions permitting complex formation between the nucleic acid molecule encoding an inward rectifier, G-protein activated, potassium channel and the nucleic acid molecule of at least 15 nucleotides capable of specifically hybridizing with the nucleic acid molecule of an isolated nucleic acid molecule encoding an inward rectifier, G-protein activated, mammalian, potassium KGA channel; (c) isolating the complex formed; and (d) separating the nucleic acid molecule encoding an inward rectifier, G-protein activated, potassium channel from the complex, thereby isolating the nucleic acid molecule encoding an inward rectifier, G-protein activated, potassium channel.

This invention further provides a method for isolating DNA encoding an inward rectifier, G-protein activated, potassium channel or a fragment thereof in a sample which comprises: (a) isolating the DNA from the sample; (b) denaturing the isolated DNA; (c) reannealing the denatured nucleic acids in the presence of two unique single stranded nucleic acid molecules of at least 15 nucleotides capable of specifically hybridizing with the nucleic acid molecule of the inward rectifier, G-protein associated, mammalian, potassium KGA channel that are complementary to nucleotide sequences on opposite strands of an isolated DNA molecule encoding an inward rectifier, G-protein activated, mammalian, potassium KGA channel; (d) polymerizing the reannealed nucleic acids with DNA polymerase under conditions that allow DNA polymerization; (e) denaturing the polymerized DNA in (d); (f) repeating steps (c) through (e) for more than 10 cycles; and (g) isolating the polymerization product in step (f). The term "unique" as used herein defines a nucleic acid molecule that does not contain known genomic repeated sequences, including but not limited to Alu sequences.

This invention provides a method for isolating DNA encoding an inward rectifier, G-protein activated, potassium channel or a fragment thereof in a sample which comprises: (a) isolating the DNA from the sample; (b) denaturing the isolated DNA; (c) reannealing the denatured nucleic acids in the presence of a unique single stranded nucleic acid molecules of at least 15 nucleotides capable of specifically hybridizing with the nucleic acid molecule of the inward rectifier, G-protein associated, mammalian, potassium KGA channel that is complementary to nucleotide sequences of an isolated DNA molecule encoding an inward rectifier, G-protein activated, mammalian, potassium KGA channel and a single stranded nucleic acid molecule encoding a known genomic repeat sequence; (d) polymerizing the reannealed nucleic acids with DNA polymerase under conditions that allow DNA polymerization; (e) denaturing the polymerized DNA in (d); (f) repeating steps (c) through (e) for more than 10 cycles; and (g) isolating the polymerization product in step (f).

This invention provides the above method for isolating from a sample a nucleic acid molecule encoding an inward rectifier, G-protein activated, potassium channel in a sample wherein, the nucleic acid molecule of at least 15 nucleotides capable of specifically hybridizing with the nucleic acid molecule of an isolated nucleic acid molecule encoding an inward rectifier, G-protein activated, mammalian, potassium KGA channel is labelled with a detectable marker.

The invention provides the nucleic acid molecule isolated by the above method for isolating from a sample a nucleic acid molecule encoding an inward rectifier, G-protein activated, potassium channel in a sample.

This invention provides a purified inward rectifier, G-protein activated, mammalian, potassium KGA channel.

This invention also provides the above-described purified channel having substantially the same amino acid sequence as the amino acid sequence shown in FIG. 5.

This invention provides a protein encoded by the above-described isolated nucleic acid molecule.

This invention provides a method for determining whether an agent activates a KGA channel which comprises: (a) contacting the host vector system of claim 10 with the agent under conditions permitting the KGA channel conductance to be affected by known ion channel agonists or intracellular second messenger agonists; and (b) detecting any change in KGA channel conductance, an increase in KGA channel conductance indicating that the agent activates the KGA channel. The term "agent" as used herein describes any molecule, protein, or pharmaceutical with the capability of directly or indirectly altering ion channel conductance by affecting second messenger systems or the ion channel directly. Agents include but are not limited to serotonin, neurotropin, enkephalins, dopamine, arachidonic acid, cholera toxin, and pertussis toxin. The term "activators" as used herein defines any agent which activates a G-protein associated receptor. The term "activates" as used herein is applied to both G-protein associated receptors and ion channel conductance and in terms of G-protein associated receptors defines the state of the receptor wherein it initiates release of a G-protein subunit which in turn initiates a cellular response. In terms of the ion channel conductance "activates" defines the state of the channel wherein the channel increases conductance. The term "deactivates" as used herein defines the state of the channel wherein the channel is initiated to decrease conductance or is incapable of conductance under conditions when the channel normally conducts ions across a membrane.

This invention also provides the agent identified by the above method.

This invention provide a pharmaceutical composition comprising an amount of the above agent effective to increase KGA conductance and a pharmaceutical acceptable carrier.

This invention provides a method for determining whether an agent deactivates KGA channel conductance which comprises: (a) contacting the host vector system for the production of a polypeptide having the biological activity of KGA channel which comprises the vector comprising the nucleic acid molecule encoding an inward rectifier, G-protein activated, mammalian, potassium KGA channel operatively linked to a promoter of RNA transcription in a suitable host with the agent under conditions permitting the KGA channel conductance to be affected by known ion channel antagonists or intracellular second messenger system agonist; and (b) detecting any change in KGA channel conductance, a decrease in KGA channel conductance indicating that the agent deactivates the KGA channel. The term "agonist" as used herein defines an agent that initiates activation of ion channel conductance or initiates activation of a second messenger system. The term "antagonist" as used herein defines an agent initiates deactivation of ion channel conductance or initiates deactivation of a second messenger system.

This invention provides agents identified by the above method for determining whether an agent deactivates KGA channel conductance.

This invention provides a pharmaceutical composition comprising an amount of the above agent effective to decrease KGA channel conductance and a pharmaceutical acceptable carrier.

This invention provides a method for identifying in a nucleic acid sample a nucleic acid molecule encoding a G-protein associated receptor which activates the inward rectifier, G-protein activated, mammalian, KGA potassium channel which comprises: (a) introducing nucleic acid molecules of claim 1 and sample to a *Xenopus* oocyte under conditions permitting expression of both the receptor and the channel; (b) contacting the oocyte of step (a) with a panel of known G-protein associated receptor activators; and (c) detecting any change in KGA channel conductance, an increase in KGA channel conductance indicating the identification of a G-protein associated receptor which activates the KGA channel.

This invention provides a method for isolating from a cDNA expression library a G-protein associated receptor which activates the inward rectifier, G-protein activated, mammalian potassium KGA channel which comprises: (a) isolating cDNA from a sample containing a number of clones of the cDNA expression library; (b) linearizing cDNA sample if necessary; (c) transcribing the linearized cDNA; (d) isolating the RNA from the transcribed cDNA; (e) introducing the isolated RNA and nucleic acid molecules of claim 1 into a *Xenopus* oocyte under conditions permitting expression of the KGA channel and G-protein associated receptor; (f) contacting the oocyte of step (e) with a panel of known G-protein associated receptor activators; (g) detecting change in KGA channel conductance; and (h) repeating steps (a) through (g) when an increase in KGA channel conductance is detected in step (g) using fewer cDNA clones from the sample until isolation of a single cDNA clone encoding a G-protein associated receptor which activates the KGA channel.

The invention provides a cDNA encoding the G-protein associated receptor isolated in the above method for isolating from a cDNA expression library a G-protein associated receptor which activates the inward rectifier, G-protein activated, mammalian potassium KGA channel.

The invention provides a G-protein associated receptor isolated in the above method for isolating from a cDNA expression library a G-protein associated receptor which activates the inward rectifier, G-protein activated, mammalian potassium KGA channel.

This invention provides a method for testing whether a G-protein associated receptor activates the inward rectifier, G-protein activated, mammalian, KGA potassium channel which comprises: (a) introducing a nucleic acid molecule of claim 1 and a nucleic acid molecule encoding the G-protein associated receptor to a *Xenopus* oocyte under conditions permitting expression of both the receptor and the channel; (b) contacting the oocyte of step (a) with a known G-protein associated receptor activator; and (c) detecting any change in KGA channel conductance, an increase in KGA channel conductance indicating that the G-protein associated receptor activates the KGA channel.

This invention provides a method for identifying in a nucleic acid sample a G-protein associated receptor capable of deactivating the inward rectifier, G-protein activated, mammalian KGA potassium channel comprising: (a) introducing nucleic acid molecule of claim 1, nucleic acid molecule of a G-protein associated receptor known to activate the KGA channel, and sample of isolated nucleic acids to a *Xenopus* oocyte under conditions permitting expression of the G-protein associated receptor that activates the KGA channel, the KGA channel and a known G-protein associated receptor; (b) contacting the oocyte of step (a) with a known G-protein associated receptor activator and a panel of known G-protein associated receptor activators; and (c) detecting any change in KGA channel conductance, a decrease in KGA channel conductance indicating the identification of an G-protein associated receptor capable of deactivating the KGA channel in the sample.

This invention provides a method for isolating from a cDNA expression library an G-protein associated receptor which deactivates the inward rectifier, G-protein activated, mammalian potassium KGA channel which comprises: (a) isolating cDNA from a sample containing a number of clones of the cDNA expression library; (b) linearizing cDNA sample if necessary; (c) transcribing the linearized cDNA; (d) isolating the RNA from the transcribed cDNA; (e) introducing the isolated RNA, nucleic acid molecule encoding a known G-protein associated receptor which activates the KGA channel, and nucleic acid molecules of claim 1 into a *Xenopus* oocyte under conditions permitting expression of the KGA channel and both receptors; (f) contacting the oocyte of step (e) with a known G-protein associated receptor activator and a panel of known inhibitory G-protein associated activators; (g) detecting any change in KGA channel conductance; and (h) repeating steps (a) through (g) when a decrease in KGA channel conductance is detected in step (g) using fewer number of cDNA clones from the sample until isolation of a single cDNA clone encoding an inhibitory G-protein associated receptor which deactivates the KGA channel.

The invention provides a cDNA encoding the G-protein associated receptor isolated by the above method for isolating from a cDNA expression library a G-protein associated receptor which deactivates the inward rectifier, G-protein activated, mammalian potassium KGA channel.

The invention provides a G-protein associated receptor capable of deactivating the inward rectifier, G-protein activated, mammalian potassium KGA channel isolated by the above method for isolating from a cDNA expression library a G-protein associated receptor which deactivates the inward rectifier, G-protein activated, mammalian potassium KGA channel.

This invention provides a method for identifying an inhibitory G-protein associated receptor which deactivates the inward rectifier, G-protein activated, mammalian KGA potassium channel comprising: (a) introducing the nucleic acid molecule encoding an inward rectifier, G-protein activated, mammalian, potassium KGA channel, a G-protein associated receptor known to activate the KGA channel, and nucleic acid molecules encoding an inhibitory G-protein associated receptor to a *Xenopus* oocyte under conditions permitting expression of both the receptors and the channel; (b) contacting the oocyte of step (b) with a known G-protein associated receptor activator and a known inhibitory G-protein associated receptor activator; and (c) detecting any change in KGA channel conductance, a decrease in KGA channel conductance indicating that the G-protein associated receptor deactivates the KGA channel.

This invention provides an antibody directed against the purified inward rectifier, G-protein activated, mammalian, potassium KGA channel. In an embodiment, this antibody is monoclonal antibody.

This invention will be better understood from the Experimental Details which follow. However, one skilled in the art will readily appreciate that the specific methods and results discussed are merely illustrative of the invention as described more fully in the claims which follow thereafter.

Experimental Materials and Methods

Preparation of RNA and oocytes. Total RNA was extracted from atria and ventricles of 19–21 day old rats of both sexes using the Chomczinski-Sacchi procedure (33). Poly (A) RNA was separated on an oligo-dT cellulose column (type 3, Collaborative Biochemical Products). Ventricle poly (A) RNA was fractionated by centrifugation (18 h, 30,000 g, 4° C.) on a linear 5%–25% sucrose gradient. *Xenopus laevis* oocytes were prepared as described (34) and injected with either 50–120 ng/oocyte poly (A) RNA, 120–200 ng/oocyte total RNA, or 35 ng/oocyte fractionated poly(A) RNA. In most cases, 5HT1A-R RNA (5–20 ng/oocyte) was co-injected with atrial or ventricle RNA. Final volume of the injected RNA solution was 50 nl. The oocytes were incubated for 3–7 days in the NDE solution (ND96 (see below) containing 1.8 Mm $CaCl_2$ and supplemented with 2.5 Mm Na-pyruvate and 50 µg/ml gentamicin). Occasionally, either 2.5–5% heat-inactivated horse serum or 0.5 mM theophylline were added to the NDE solution. Incubation of oocytes in pertussis toxin (PTX; List Biochemicals) was done in NDE solution without the addition of pyruvate, serum or theophylline. cDNAs of 5HT1A receptor (see 23) and $G_{i2}\alpha$ (a gift from M. I. Simon, Caltech) in pBluescript were linearized, and RNA was synthesized in vitro as described (34).

Electrophysiological recordings were performed using the two electrode voltage clamp method with the Dagan 8500 amplifier (Dagan Instruments, Minneapolis) as described (35). The oocytes were usually kept in the ND96 solution: 96 mM NaCl/2 mM KCl/1 mM $MgCl_2$/1 mM $CaCl_2$/5 mM Hepes, pH=7.5. Most measurements were done in the high $K^+$ solution (hK): 96 mM KCl/2 mM NaCl/1 mM $MgCl_2$/1 mM $CaCl_2$/5 mM Hepes, pH=7.5. Solutions containing intermediate concentrations of $K^+$ were made by substituting $K^+$ for $Na^+$. Solution exchange and drug application were done by superfusing the cell placed in a 0.5 ml chamber. GDP-β-S(trilithium salt; Sigma) was injected by pressure (35). Stimulation, data acquisition, and analysis were performed using pCLAMP software (Axon Instruments, Foster City, Calif.).

Experimental Results

To express the KG channel, the oocytes were injected with atrial total or poly(A) RNA. In order to avoid the possibility that a low level of expression of the muscarinic receptor will make undetectable even a well-expressed KG channel, atrial RNA was usually supplemented with mRNA coding for the serotonin-5HT1A receptor (5HT1A-R); oocytes injected with this RNA mixture will be termed RNA-injected oocytes throughout the paper. When expressed in atrial myocytes, the 5HT1A-R efficiently coupled to the KG channel normally existing in these cells (23), and it was expected to do so in the oocytes.

Four to 5 days after RNA injection addition of 10 μM ACh or 1–2 μM 5HT to the ND96 bath solution did not cause any significant change in membrane current. Therefore, the effects of ACh and 5HT were tested in a high potassium (hK) solution with 96 mM $K^+$ and 2 mM $Na^+$. In this solution, the $K^+$ equilibrium potential ($E_K$) is close to 0 mV, and this enables inward $K^+$ current flow through inwardly rectifying K channels at negative holding potentials (–80 mV was routinely used in this study).

Changing ND 96 to the hK solution was accompanied by the development of an inward current that reached a steady level within 0.5–1 min ($I_{hK}$; FIG. 1A). $I_{hK}$ was also observed in native (not injected with any RNA) oocytes, or in oocytes injected with 5HT1A-R RNA alone, but it was always larger in RNA-injected oocytes (P<0.001, two-tailed t-test; Table 1).

Table 1

Inward currents evoked by high $K^+$ and by 5HT. The entries are inward currents in nA shown as mean±SEM (n), measured at –80 mV in the hK solution. 5HT concentration ranged in different experiments from 100 nM to 2 μM.

| Injected RNA | $I_{hK}$ | $I_{5HT}$ |
|---|---|---|
| None (native oocytes) | 72 ± 6 (34) | 0 (18) |
| 5HT1A-R | 54 ± 4 (11) | 0 (12) |
| Atrial + 5HT1A-R | 123 ± 8 (55) | 290 ± 43 (55) |

Figure 1B:
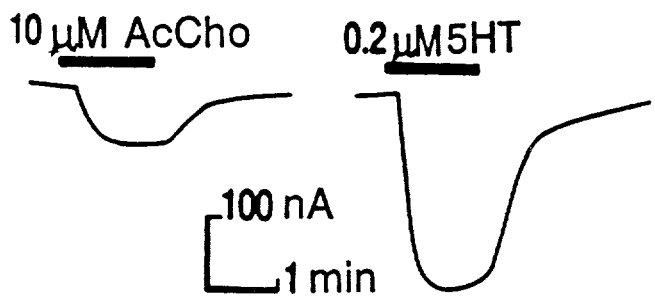

In RNA-injected oocytes, application of 5HT or ACh in hK solution induced an inward current ($I_{5HT}$) that subsided upon washout of the transmitter (FIG. 1A, B). The response to ACh was usually smaller than to 5HT when measured in the oocytes of the same frog (FIG. 1B). Thus, in oocytes of one frog $I_{5HT}$ was 1102±84 nA (n=6), whereas the ACh response was 382±45 nA(n=6). $I_{5HT}$ tended to decrease on repeated applications of 5HT, and this could be overcome by increasing the intervals between applications to 10 min or more, suggesting the presence of a desensitization process. $I_{5HT}$ and an increased (in comparison with native oocytes) $I_{hK}$ were also observed in oocytes injected with ventricle poly (A) RNA+5HT1A-R RNA, but the $I_{5HT}$ was about 20 times smaller than with atrial poly(A) RNA (not shown). 5HT had no effect in oocytes injected with atrial RNA without the 5HT1A-R RNA (n=4) or with 5HT1A-R RNA alone, or in native oocytes (Table 1).

Figure 1C:
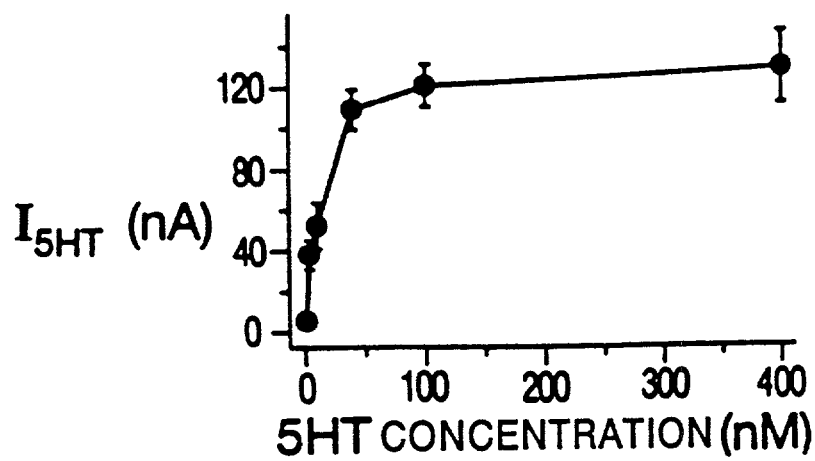

The 5HT dose-response curve showed saturation at about 100 nM and a half-maximal response at about 15 nM (FIG. 1C), which is characteristic of the 5HT1 receptor class (36). A similar current was evoked by a selective 5HT1A agonist, 8-OH DPAT (8-OH-2(D1-n-(propylamino)-tetralin; data not shown).

Figure 2A:
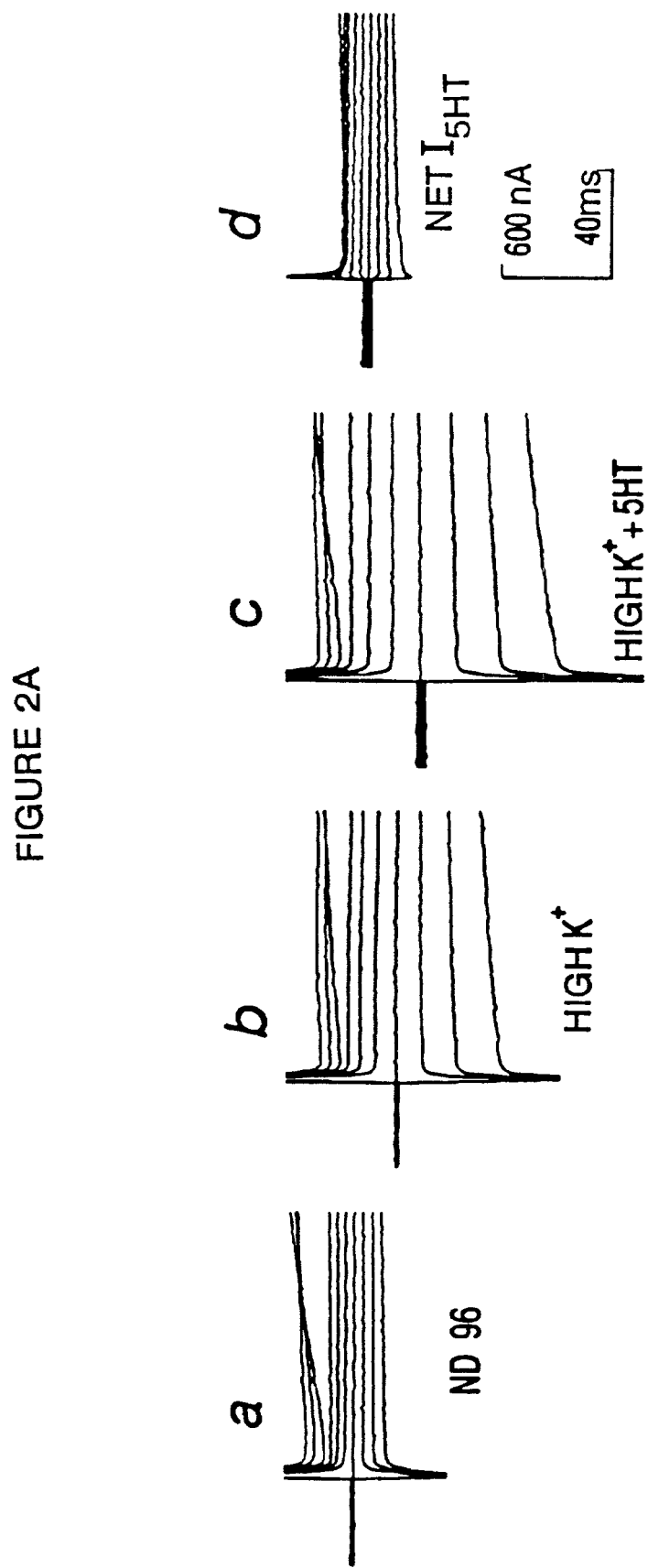
FIG. 2. $I_{hk}$ and $I_{5HT}$ are inwardly rectifying $K^+$ currents. (A) Currents evoked by voltage steps from the holding potential of −80 mV to voltages between −140 and 40 mV in 20 mV steps in ND96(a), hK (b), hK in the presence of 5HT (c). Net $I_{5HT}$ (d) was obtained by digital subtraction of (b) from (c). (B) Current-voltage relations of the total membrane current in a representative oocyte in NG 96 (2 mM [Kout]; □), in 25 mM [K⁺out] (◆); in 75 mM [Kout] (○), and in hK (96 mM [Kout]; ▲). (C) Current-voltage relation of the net $I_{5HT}$ in the same oocyte as in (B) in 25 mM [Kout] (◆), 75 mM [Kout] (○), and 96 mM [Kout] (▲). (D) The dependence of the reversal potentials of total membrane current (▲) and of $I_{5HT}$ (◆) on [Kout]. The straight lines represent least square fits to data (mean±SEM, n=3 for each point).
Figure 2B:
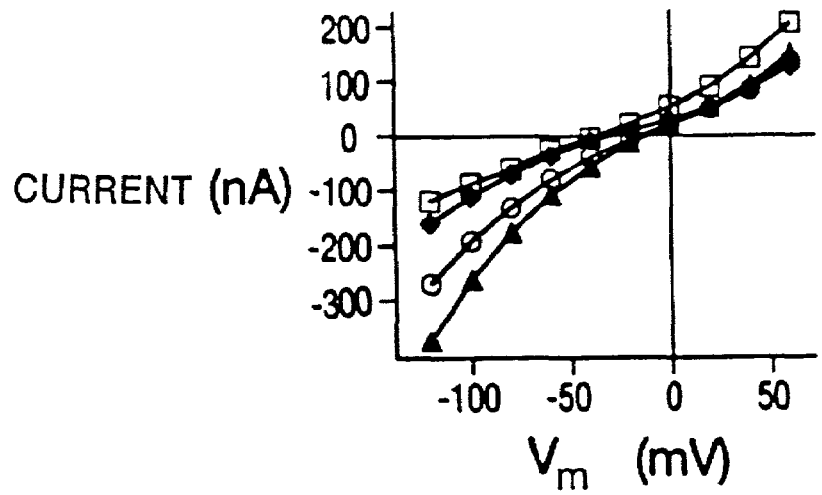
Figure 2C:
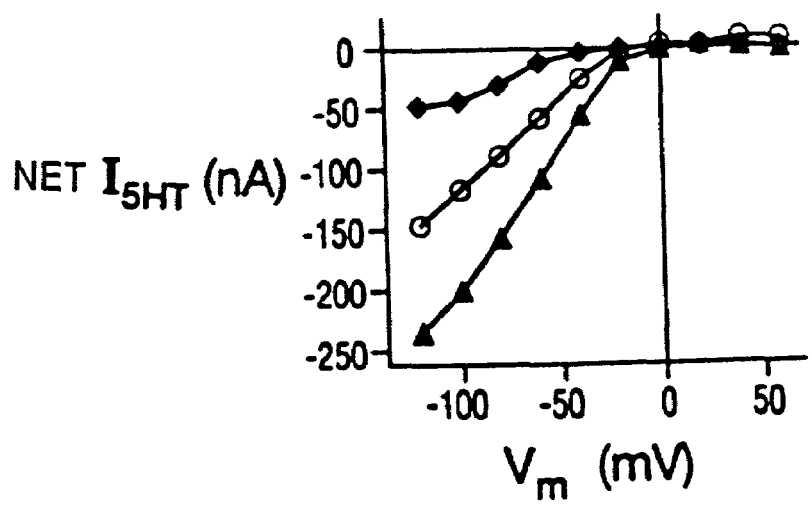
Figure 2D:
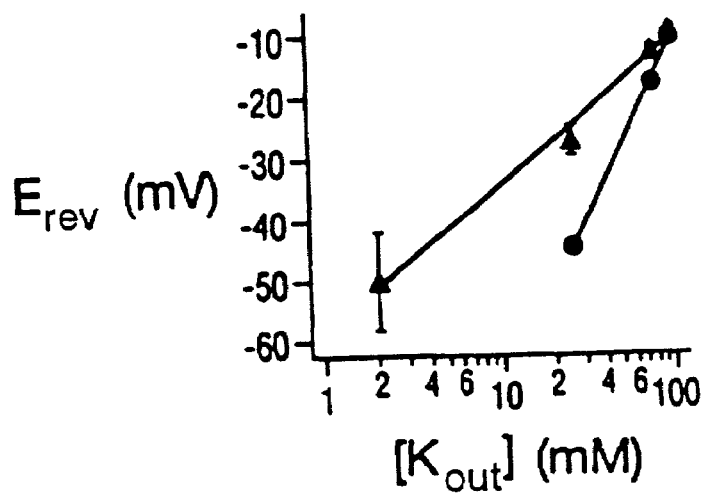

The current-voltage (I–V) characteristic of the oocyte membrane was studied by applying voltage steps from a holding potential of –80 mV. In normal ND96, in the range –140–-20 mV, only voltage- and time-independent "leak" currents were observed (FIG. 2a), and the I–V curve was linear (FIG. 2B). Above –20 mV, a slowly developing outward current was observed (FIG. 2A, a–c); this is known to be due to opening of a $Cl^-$ channel activated by $Ca^{2+}$ entry through voltage-dependent $Ca^{2+}$ channels (37). The $Ca^{2+}$-activated $Cl^-$ current was also seen in the hK solution; in addition, the total membrane current evoked by steps to –120 and up to –20 mV was larger than in ND96 (FIG. 2Ab; 2B), whereas above 0 mV there was little or no change. This suggested that most or all of $I_{hK}$ elicited at –80 mV by the exchange of ND96 to hK solution was due to a $K^+$ current flowing through a constitutively active inward rectifier $K^+$ channel(s). This current showed some time-dependent inactivation at –140 mV (FIG. 2Ab) and at more negative potentials (not shown); this inactivation phenomenon was not studied further. In the presence of 5HT, the membrane currents between –140 and –20 mV were further increased (FIG. 2Ac). Net 5HT-evoked currents, obtained by digital subtraction of total membrane currents in the absence of 5HT from currents in its presence (FIG. 2Ad), showed clear inward rectification; the 5HT-activated channels conducted little or no current above $E_K$ at different external $K^+$ concentrations, $[K_{out}]$ (FIG. 2C). The extrapolated reversal potential of $I_{5HT}$ showed an almost perfect selectivity of the 5HT-activated channel to $K^+$, changing by about 58 mV per 10-fold change in $[K_{out}]$ (FIG. 2D). The reversal potential of the total membrane current in the absence of 5HT also depended on $[K_{out}]$ (FIG. 2B) but changed only by 24 mV per tenfold change in $[K_{out}]$ (FIG. 2D). This does not necessarily imply poor ion selectivity of the constitutively active inward rectifier, but may reflect the relatively high contribution of $Cl^-$ and $Na^+$ to the resting membrane conductance (38).

Figure 3D:
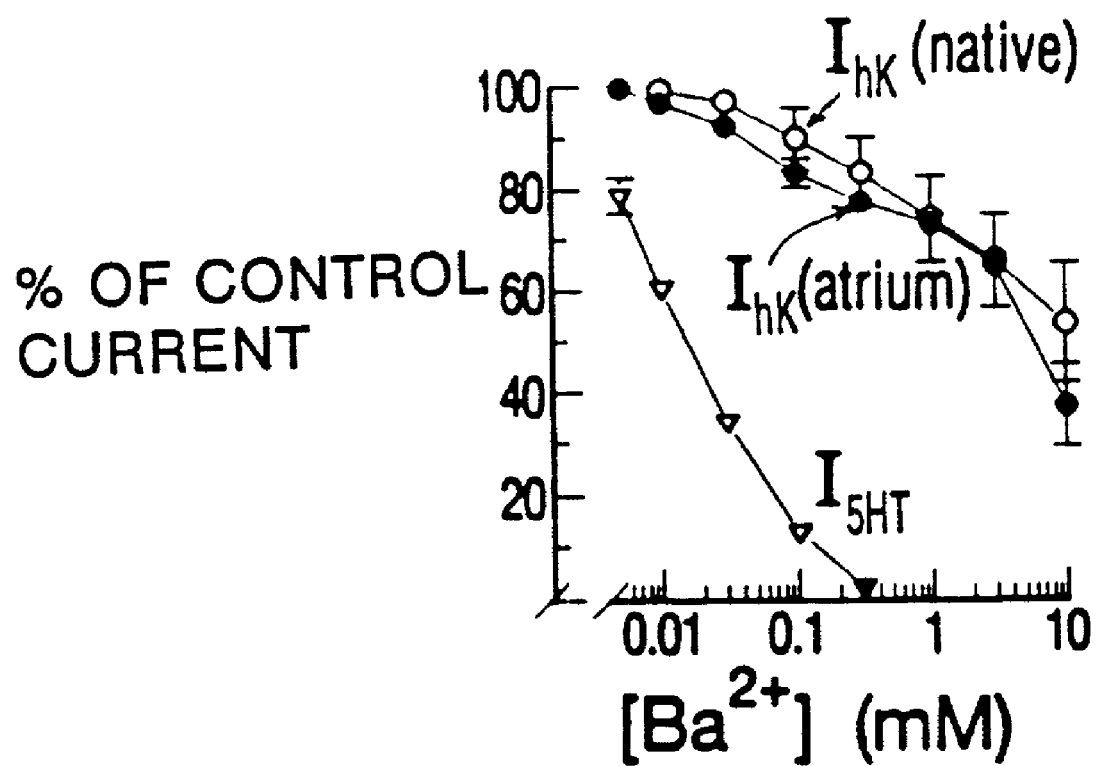
FIG. 3. $Ba^{2+}$ block of $I_{hk}$ and $I_{5HT}$. (A–C), records taken from the same oocyte at 10 min intervals. Between the records, the cell was bathed in ND96. 5HT concentration was 4 nM. Note that in (B) 300 μM $Ba^{2+}$ reduces $I_{hK}$ and almost completely blocks $I_{5HT}$. $Ba^{2+}$ and 5HT were washed out simultaneously, and this resulted in an inward current "tail". (D) dose dependence of $Ba^{2+}$ inhibition of $I_{hK}$ in native oocytes (○), $I_{hK}$ in RNA-injected oocytes (●), $I_{5HT}$ in RNA-injected oocytes (∇). Data are mean±SEM, n=3 to 7 for each point.

Block by external $Ba^{2+}$ is one of the characteristic features of inward rectifiers (24). In normal ND96 solution, $Ba^{2+}$ (5 μM-3 mM) did not cause any significant changes in resting current or conductance in native or RNA-injected oocytes at the holding potential of –80 mV. In the hK solution, $Ba^{2+}$ inhibited both $I_{hK}$ and $I_{5HT}$ (FIG. 3), and this was accompanied by a decrease in membrane conductance (not shown). 300 μM, $Ba^{2+}$ blocked about 20% of $I_{hK}$ but almost completely abolished $I_{5HT}$ (FIG. 3B). The $IC_{50}$ (half-inhibition concentration) for $Ba^{2+}$ block of $I_{5HT}$ was about 15 µM, whereas $IC_{50}$ for $I_{hK}$ block was above 3 mM (FIG. 3D). It is noteworthy that, although the sensitivity of $I_{hK}$ to $Ba^{2+}$ block was similar in native and RNA-injected oocytes, the latter did appear to have a small component of $I_{hK}$ inhibited by low doses of $Ba^{2+}$ (FIG. 3D). This raises the possibility that the atrial $I_{hK}$ is more sensitive to $Ba^{2+}$ block than the oocyte's $I_{hK}$, or that a fraction of the highly $Ba^{2+}$-sensitive channels underlying $I_{5HT}$ could be active in the absence of agonist. Note also that there was an inward current "tail" observed when $Ba^{2+}$ and 5HT was washed out simultaneously (FIG. 3B), presumably because the rate-limiting step in deactivation of the channel proceeds more slowly than unblock from $Ba^{2+}$.

To estimate the size of RNA encoding the expressed inward rectifiers, ventricle poly(A) RNA (available in large amounts) was fractionated on a sucrose gradient. The size distribution of the fractions was measured by RNA gel blots probed with [$^{32}$P]-labeled poly(T) (39). The RNA encoding $I_5HT$ was found mainly in two size fractions covering the range between 2.5 and 5.5 kb. The peak expression of ventricle $I_{hK}$ was in lower size fractions, in the 1.5–3 kb range (data not shown).

Figure 4A:
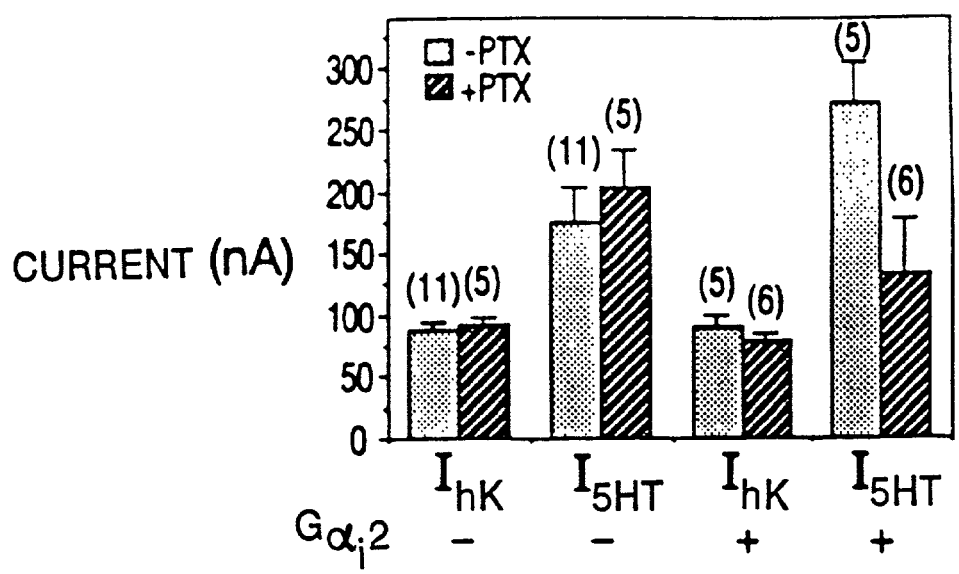
FIG. 4. $I_{5HT}$ is mediated by activation of a G-protein. (A) The effect of PTX treatment (500 ng/ml, 20–26 h) on $I_{hK}$ and $I_{5HT}$. The cells were injected with 120 ng/oocyte total atrial RNA, 11 ng/oocyte 5HT1A-R RNA, and, where indicated, with 11 ng/oocyte $G_{i2}α$ RNA. (B) GDP-β-S injection inhibits $I_{5HT}$ but not $I_{hK}$ in an oocyte injected with atrial+ 5HT1A-R RNAs. 5HT concentration was 0.4 μM. A small outward current deflection (denoted by ⋆) upon washout of 5HT was caused by an inadvertent perfusion of ND96 for a few seconds.
Figure 4B:
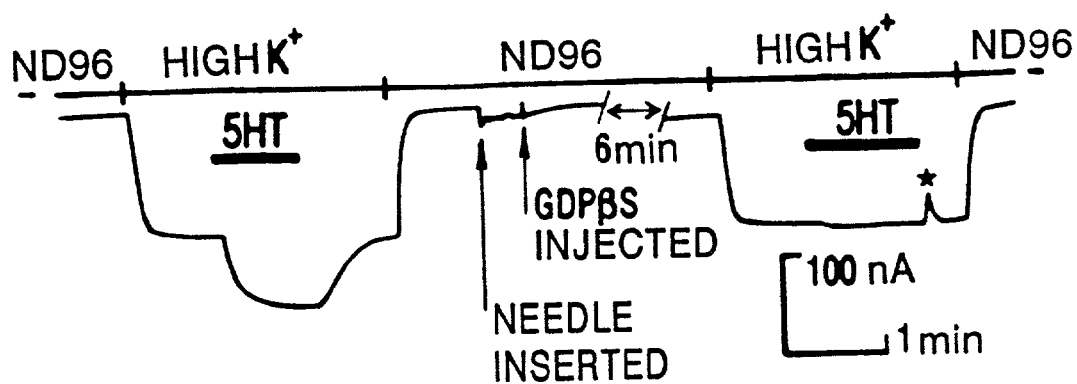

In atrium, the muscarinic receptor is coupled to the KG channel via a PTX-sensitive G-protein (8). Surprisingly, in RNA-injected oocytes, $I_{5HT}$ was not affected by treatment with PTX; neither was $I_{hK}$ (FIG. 4A). To test whether the 5HT1A receptor couples to the $K^+$ channel via a G-protein, the oocytes were injected with 400–800 pmole/oocyte of the non-hydrolysable analog of GDP, GDP-β-S, that is known to inhibit the activity of PTX-sensitive as well as of PTX-insensitive G-proteins (40). In 4 cells, GDP-β-S injection had no effect on $I_{hK}$ (115±8% of control) but strongly inhibited $I_{5HT}$, to 4±1% of control (FIG. 4B). Thus, it appears that the coupling between the 5HT1A receptor and the KG channel occurs via an oocyte's endogenous PTX-insensitive G-protein.

We examined whether an overexpressed PTX-sensitive α subunit of a G-protein, e.g. $G_{i2}α$, could compete with the "native" PTX-insensitive α subunit for the expressed 5HT1A receptor, thus restoring the PTX sensitivity of the KG channel activation. As shown in FIG. 4A, in oocytes injected with atrial RNA plus cRNAs encoding 5HT1A-R and $G_{i2}α$, PTX inhibited $I_{5HT}$ by about 50% (P<0.01, two-tailed t-test), whereas $I_{hK}$ was unaffected.

Experimental Discussion

The present results demonstrate for the first time that the atrial inward rectifier $K^+$ (KG) channel, which in the native tissue is activated by ACh via a PTX-sensitive G-protein, is expressed in oocytes injected with atrial RNA. Current through the channel can be activated by acetylcholine (ACh) or, if RNA encoding a neuronal 5HT1A receptor in co-injected with atrial RNA, by serotonin (5HT). Activation of the channel probably occurs via a muscarinic ACh receptor synthesized following atrial RNA injection, rather than via the oocyte's endogenous muscarinic receptor. The latter couples to phospholipase C, and its activation induces very characteristic large transient Cl⁻ current responses caused by $Ca^{2+}$ release from intracellular stores (41). Fortunately, the majority of oocyte batches lose this response after defolliculation (42), and this response was not observed in the present study. Because the ACh-evoked currents were small in most cases, we concentrated on the study of the 5HT response; the latter was undoubtedly mediated by the introduced 5HT1A receptor, as 5HT was ineffective in oocytes not injected with 5HT1A-RNA, and the response displayed the expected pharmacological properties.

The evidence presented here indicates that, in oocytes injected with atrial and 5HT1A-R RNAs, activation of the 5HT1A receptor leads to opening of a $K^+$ channel that bears distinctive features of an anomalous rectifier, similar to those of the atrial KG: i) it conducts inward but not outward $K^+$ current; ii) it is blocked by low concentrations of $Ba^{2+}$, iii) the conductance of the channel does not depend solely on voltage but on ($E-E_K$). The expression of this channel must truly be directed by atrial RNA, because: i) no hormone or transmitter-activated current of this kind is observed in native oocytes; ii) expression of 5HT1A receptor alone does not cause the appearance of such a response. Based on ventricle RNA fractionation data, the RNA encoding the 5HT-activated channel is in a broad size range between 2.5 and 5.5 kb. This is similar or somewhat smaller than the reported 4–5 kb mRNA size of some constitutively active inward rectifiers expressed in Xenopus oocytes (43, 44), as well as of the cloned IRK1 (5.5 kb; ref. 31) and ROMK1 (4 kb; ref. 30) channels. The properties of $I_{5HT}$ directed by ventricle and atrial RNA are very similar, and it is reasonable to assume that they are encoded by the same RNA species.

Opening of the inward rectifier by 5HT is mediated by activation of a G-protein, as expected for the KG channel, because i) 5HT1A receptor belongs to the family of 7-helix receptors all of which act via G-proteins (40); ii) $I_{5HT}$ was inhibited by intracellular injection of GDP-β-S. However, the G-protein participating in this pathway was PTX-insensitive, possibly an endogenous oocyte G-protein. It is not clear why in the oocyte the channel activation pathway involves a PTX-insensitive G-protein. The atrial KG channel normally couples to $G_i$ (9), and there are at least two subspecies of $G_i$ in the oocyte (45); also, some $G_i$ may be expressed from atrial RNA. Also, in the hippocampus, the 5HT1A receptor opens a $K^+$ channel by activating a PTX-sensitive G-protein (21). One possibility is that a vast excess of this undefined PTX-insensitive G-protein overrides the others in competition for coupling to the 5HT1A receptor. Whatever the reason for this unexpected coupling, our results show that the PTX sensitivity of the KG channel activation can be partially restored by overexpression of the α subunit of $G_i$. Since the actual identify of the α subunit does not seem to be important for activation of the expressed KG channel, these results imply that the βγ subunit complex doublet may be the activator of the channel in this case (cf. 10, 11).

Atrial and ventricle RNAs also induce an enhanced activity of an additional inward rectifier, that is active in the absence of any specific stimulation (referred to as $I_{hK}$ in this paper). $I_{hK}$ in atrial RNA-injected oocytes is about twice as large as in native oocytes or oocytes injected with 5HT1A-R RNA alone. This current does not appear to represent the "basal" activity of the same channel activated by 5HT or ACh because it has a much lower sensitivity to $Ba^{2+}$ block. Moreover, the fractionation data indicates that the RNA directing the expression of $I_{hK}$ is smaller than that encoding the KG channel. However, it is not clear whether this atrial (or ventricle) RNA encodes the channel itself or a factor that enhances the expression or the activity of a native channel. Further studies, such as expression cloning, will help to identify the messages encoding the two inward rectifiers whose expression is reported here.

REFERENCES

1. Sakmann, B., Noma, A. & Trautwein, W. (1983) Nature 303:250–253.
2. Ijima, T., Irisawa, H. & Kameyama, M. (1985) J. Physiol. (London) 359:485–501.
3. Pfaffinger, P. G., Martin, J. M., Hunter, D. D., Nathanson, N. M. & Hille, B. (1985) Nature 317:536–538.
4. Breitweiser, G. E. & Szabo, G. (1985) Nature 317: 538–540.
5. Kurachi, Y., Nakajima, T. & Sugimoto, T. (1986) Am. J. Physiol. 251:H681–H684.
6. Yatani, A., Codina, J., Brown, A. M. & Birnbaumer, L. (1987) Science 235:207–211.
7. Yatani, A., Mattera, R., Codina, J., Graf, R., Okane, K., Pardell, E., Iyengar, R., Brown, A. M. & Birnbaumer, L. (1988) Nature 336:680–682.
8. Kurachi, Y., Tung, R. T., Ito, H. & Nakajima, T. (1992) Prog. Neurobiol. 39:229–246.
9. Brown, A. M. & Birnbaumer, L. (1990) A. Rev. Physiol. 52:197–213.
10. Logothetis, D. E., Kurachi, Y., Galper, J., Neer, E. J. & Clapham, D. E. (1987) Nature 325:321–326.
11. Kurachi, Y., Ito, H., Sugimoto, T., Katada, T. & Ui, M. (1989) Pflugers Arch. 413:325–327.
12. Codina, J., Yatani, A., Grenet, D., Brown, A. M. & Birnbaumer, L. (1987) Siecence 236–442–445.
13. Ito, H., Tung, T. T., Sugimoto, T., Kobayashi, I., Takahashi, K., Katada, T., Ui, M. & Kurachi, Y. (1992) J. Gen. Physiol. 99:961–983.
14. Kim, D., Lewis, D. L., Graziadei, L., Neer, E. J., Bar-Sagi, D. & Clapham, D. E. (1989) Nature 337: 557–560.
15. Kurachi, Y., Nakajima, T., & Sugimoto, T. (1986) Pflugers Arch. 407:264–276.
16. Friel, D. D. & Bean, B. P. (1990) Pflugers Arch. 415:651–657.
17. Kurachi, Y., Ito, H., Sugimoto, T., Shimizu, T., Miki, I. & Ui, M. (1989) Pflugers Arch. 414:102–104.
18. Codina, J., Grenet, D., Yatani, A., Birnbaumer, L. & Brown, A. M. (1987) FEBS Letters, 216:104–106.
19. North, R. A., Williams, J. T., Suprenant, A. & Christie, M. J. (1987) Proc. Natl. Acad. Sci. USA 84:5487–5491.
20. Andrade, R., Malenka, R. C. & Nicoll, R. A. (1986) Science 234:1261–1265.
21. Andrade, R. & Nicoll, R. A. (1987) J. Physiol. 394: 99–124.
22. VanDongen, A. M. J., Codina, J., Olate, J., Mattera, R., Joho, R., Birnbaumer, L. & Brown, A. M. (1988) Science 242:1433–1437.
23. Karschin, A., Ho, B. Y., Labarca, G., Elroy-Stein, O., Moss, B., Davidson, N. & Lester, H. A. (1991) Proc. Natl. Acad. Sci. USA 88:5694–5698.
24. Hille, B. (1992) *Ionic Channels of Excitable Membranes,* 2nd edition (Sinauer, Sunderland, Mass.).
25. Horie, M. & Irisawa, H. (1987) Am. J. Physiol. 253: H210–H214.
26. Ciani, S., Krasne, S., Myazaki, S. & Hagiwara, S. (1978) J. Membr. Biol. 44:103–134.
27. Silver, M. R. & DeCoursey, T. E. (1990) J. Gen. Physiol. 96:109–133.
28. Sentenac H., Bonneaud N., Minet M., Lacroute F., Salmon J. -M., Gaymard F. & Grignon C. (1992) Science 256:663–665.
29. Anderson J. A., Huprikar S. S., Kochian L. V., Lucas W. J. & Gaber R. F. (1992) Proc. Natl. Acad. Sci. USA 89:3736–3740.
30. Ho, K., Nichols, C. G., Lederer, W. J., Lytton, J., Vassilev, P. M., Kanazirska, M. V. & Hebert, S. C. (1993) Nature 362:31–38.
31. Kubo, Y., Baldwain, T. J., Jan, Y. N. & Jan, L. Y. (1993) Nature 362:127–132.
32. Aldrich, R. (1993) Nature 362:107–108.
33. Chomczinski, P. & Sacchi, N. (1987) Anal. Biochem. 162:156–159.
34. Dascal, N. & Lotan, I. (1992) in *Methods in Molecular Biology, v.* 13: *Protocols in Molecular Neurobiology,* eds. Longstaff, A & Revest, P. (Humana Press, Totowa, N.J.).
35. Dascal, N., Ifune, C., Hopkins, R., Snutch, T. P., Lubbert, H., Davidson, N., Simon, M., & Lester, H. A. (1986) Mol. Brain Res. 1:201–209.
36. Hoyer, D. & Schoeffer, P. (1991) J. Recept. Res. 11:197–214.
37. Barish, M. E. (1983) J. Physiol. (London) 342:309–325.
38. Dascal, N., Landau, E. M. & Lass, Y. (1984) J. Physiol. (London) 352:551–574.
39. Lubbert, H., Snutch, T. P., Dascal, N., Lester, H. A. & Davidson, N. (1987) J. Neurosci. 7:1159–1165.
40. Gilman, A. G. (1987) A. Rev. Biochem. 56:615–649.
41. Dascal, N. (1987) CRC Crit. Rev. Biochem. 22:317–387.
42. Miledi, R. & Woodward, R. M. (1989) J. Physiol. 416:601–621.
43. Lewis, D. L., Ikeda, S. R., Aryee, D. & Joho, R. H. (1991) FEBS Lett. 290:17–21.
44. Perier, F., Coulter, K. L., Radeke, C. M. & Vanderberg, C. A. (1992) J. Neurochem. 59:1971–1974.
45. Olate, J., Martinez, S., Purcell, P., Jorguera, H., Codina, J., Birnbaumer, L. & Allende, J. E. (1990) FEBS Lett. 268:27–31.

What is claimed is:

1. A method for isolating a nucleic acid molecule encoding an inward rectifier, G-protein activated, potassium channel from a sample comprising:
   (a) isolating nucleic acids from the sample;
   (b) contacting the isolated nucleic acids with a nucleic acid probe having a sequence comprising at least 15 nucleotides of SEQ ID NO:1 or complement thereof under conditions permitting the formation of a complex between said nucleic acid probe and a nucleic acid molecule encoding an inward rectifier, G-protein activated, potassium channel in said isolated nucleic acids, wherein the nucleic acid probe specifically hybridizes with the nucleic acid sequence of SEQ ID NO: 1 or complements thereof;
   (c) isolating the complex;
   (d) separating the nucleic acid molecule encoding an inward rectifier, G-protein activated, potassium channel from the nucleic acid probe; and
   (e) assaying the protein encoded by the nucleic acid molecule for a biological activity of the inward rectifier, G-protein activated, potassium channel encoded by SEQ ID NO:1.

2. A method of claim 1, wherein the nucleic acid probe is labeled with a detectable marker.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2076 base pairs
      (B) TYPE: nucleic acid
      (C) STRANDEDNESS: single
      (D) TOPOLOGY: linear (ii) MOLECULE TYPE: cDNA (ix) FEATURE:
    (A) NAME/KEY: CDS
    (B) LOCATION: 32..1534

(xi) SEQUENCE DESCRIPTION: SEQ ID NO: 1:

```
GGCACGAGAA TCTGGATCTC CCCTCCGTAT T ATG TCT GCA CTC CGA AGG AAA         52
                                  Met Ser Ala Leu Arg Arg Lys
                                   1               5

TTT GGG GAC GAT TAC CAG GTA GTG ACC ACT TCG TCC AGC GGT TCG GGC       100
Phe Gly Asp Asp Tyr Gln Val Val Thr Thr Ser Ser Ser Gly Ser Gly
             10                  15                  20

TTG CAG CCC CAG GGG CCA GGA CAG GGC CCA CAG CAG CAG CTT GTA CCC       148
Leu Gln Pro Gln Gly Pro Gly Gln Gly Pro Gln Gln Gln Leu Val Pro
 25                  30                  35

AAG AAG AAA CGG CAG CGG TTC GTG GAC AAG AAC GGT CGG TGC AAT GTG       196
Lys Lys Lys Arg Gln Arg Phe Val Asp Lys Asn Gly Arg Cys Asn Val
 40                  45                  50                  55

CAG CAC GGC AAC CTG GGC AGC GAG ACC AGT CGC TAC CTT TCC GAC CTC       244
Gln His Gly Asn Leu Gly Ser Glu Thr Ser Arg Tyr Leu Ser Asp Leu
                 60                  65                  70

TTC ACT ACC CTG GTG GAT CTC AAG TGG CGT TGG AAC CTC TTT ATC TTC       292
Phe Thr Thr Leu Val Asp Leu Lys Trp Arg Trp Asn Leu Phe Ile Phe
             75                  80                  85

ATC CTC ACC TAC ACC GTG GCC TGG CTC TTC ATG GCG TCC ATG TGG TGG       340
Ile Leu Thr Tyr Thr Val Ala Trp Leu Phe Met Ala Ser Met Trp Trp
         90                  95                 100

GTG ATC GCT TAT ACC CGG GGC GAC CTG AAC AAA GCC CAT GTC GGC AAC       388
Val Ile Ala Tyr Thr Arg Gly Asp Leu Asn Lys Ala His Val Gly Asn
    105                 110                 115

TAC ACT CCC TGT GTG GCC AAT GTC TAT AAC TTC CCC TCT GCC TTC CTT       436
Tyr Thr Pro Cys Val Ala Asn Val Tyr Asn Phe Pro Ser Ala Phe Leu
120                 125                 130                 135

TTC TTC ATC GAG ACC GAG GCC ACC ATC GGC TAT GGC TAC CGC TAC ATC       484
Phe Phe Ile Glu Thr Glu Ala Thr Ile Gly Tyr Gly Tyr Arg Tyr Ile
                140                 145                 150

ACC GAC AAG TGC CCC GAG GGC ATC ATC CTT TTC CTT TTC CAG TCC ATC       532
Thr Asp Lys Cys Pro Glu Gly Ile Ile Leu Phe Leu Phe Gln Ser Ile
            155                 160                 165

CTT GGC TCC ATC GTG GAC GCT TTC CTC ATC GGC TGC ATG TTC ATC AAG       580
Leu Gly Ser Ile Val Asp Ala Phe Leu Ile Gly Cys Met Phe Ile Lys
        170                 175                 180

ATG TCC CAG CCC AAA AAG CGC GCC GAG ACC CTC ATG TTT AGC GAG CAT       628
Met Ser Gln Pro Lys Lys Arg Ala Glu Thr Leu Met Phe Ser Glu His
    185                 190                 195

GCG GTT ATT TCC ATG AGG GAC GGA AAA CTC ACT CTC ATG TTC CGG GTG       676
Ala Val Ile Ser Met Arg Asp Gly Lys Leu Thr Leu Met Phe Arg Val
200                 205                 210                 215

GGC AAC CTG CGC AAC AGC CAC ATG GTC TCC GCG CAG ATC CGC TGC AAG       724
Gly Asn Leu Arg Asn Ser His Met Val Ser Ala Gln Ile Arg Cys Lys
                220                 225                 230

CTG CTC AAA TCT CGG CAG ACA CCT GAG GGT GAG TTT CTA CCC CTT GAC       772
Leu Leu Lys Ser Arg Gln Thr Pro Glu Gly Glu Phe Leu Pro Leu Asp
            235                 240                 245

CAA CTT GAA CTG GAT GTA GGT TTT AGT ACA GGG GCA GAT CAA CTT TTT       820
Gln Leu Glu Leu Asp Val Gly Phe Ser Thr Gly Ala Asp Gln Leu Phe
        250                 255                 260

CTT GTG TCC CCT CTC ACC ATT TGC CAC GTG ATC GAT GCC AAA AGC CCC       868
Leu Val Ser Pro Leu Thr Ile Cys His Val Ile Asp Ala Lys Ser Pro
```

```
                265                 270                 275
TTT TAT GAC CTA TCC CAG CGA AGC ATG CAA ACT GAA CAG TTC GAG GTG       916
Phe Tyr Asp Leu Ser Gln Arg Ser Met Gln Thr Glu Gln Phe Glu Val
280                 285                 290                 295

GTC GTC ATC CTG GAA GGC ATC GTG GAA ACC ACA GGG ATG ACT TGT CAA       964
Val Val Ile Leu Glu Gly Ile Val Glu Thr Thr Gly Met Thr Cys Gln
                300                 305                 310

GCT CGA ACA TCA TAC ACC GAA GAT GAA GTT CTT TGG GGT CAT CGT TTT      1012
Ala Arg Thr Ser Tyr Thr Glu Asp Glu Val Leu Trp Gly His Arg Phe
            315                 320                 325

TTC CCT GTA ATT TCT TTA GAA GAA GGA TTC TTT AAA GTC GAT TAC TCC      1060
Phe Pro Val Ile Ser Leu Glu Glu Gly Phe Phe Lys Val Asp Tyr Ser
        330                 335                 340

CAG TTC CAT GCA ACC TTT GAA GTC CCC ACC CCT CCG TAC AGT GTG AAA      1108
Gln Phe His Ala Thr Phe Glu Val Pro Thr Pro Pro Tyr Ser Val Lys
    345                 350                 355

GAG CAG GAA GAA ATG CTT CTC ATG TCT TCC CCT TTA ATA GCA CCA GCC      1156
Glu Gln Glu Glu Met Leu Leu Met Ser Ser Pro Leu Ile Ala Pro Ala
360                 365                 370                 375

ATA ACC AAC AGC AAA GAA AGA CAC AAT TCT GTG GAG TGC TTA GAT GGA      1204
Ile Thr Asn Ser Lys Glu Arg His Asn Ser Val Glu Cys Leu Asp Gly
                380                 385                 390

CTA GAT GAC ATT AGC ACA AAA CTT CCA TCG AAG CTG CAG AAA ATT ACG      1252
Leu Asp Asp Ile Ser Thr Lys Leu Pro Ser Lys Leu Gln Lys Ile Thr
            395                 400                 405

GGG AGA GAA GAC TTT CCC AAA AAA CTC CTG AGG ATG AGT TCT ACA ACT      1300
Gly Arg Glu Asp Phe Pro Lys Lys Leu Leu Arg Met Ser Ser Thr Thr
        410                 415                 420

TCA GAA AAA GCC TAT AGT TTG GGT GAT TTG CCC ATG AAA CTC CAA CGA      1348
Ser Glu Lys Ala Tyr Ser Leu Gly Asp Leu Pro Met Lys Leu Gln Arg
    425                 430                 435

ATA AGT TCG GTT CCT GGC AAC TCT GAA GAA AAA CTG GTA TCT AAA ACC      1396
Ile Ser Ser Val Pro Gly Asn Ser Glu Glu Lys Leu Val Ser Lys Thr
440                 445                 450                 455

ACC AAG ATG TTA TCA GAT CCC ATG AGC CAG TCT GTG GCC GAT TTG CCA      1444
Thr Lys Met Leu Ser Asp Pro Met Ser Gln Ser Val Ala Asp Leu Pro
                460                 465                 470

CCG AAG CTT CAA AAG ATG GCT GGA GGA CCT ACC AGG ATG GAA GGG AAT      1492
Pro Lys Leu Gln Lys Met Ala Gly Gly Pro Thr Arg Met Glu Gly Asn
            475                 480                 485

CTT CCA GCC AAA CTA AGA AAA ATG AAC TCT GAC CGC TTC ACA              1534
Leu Pro Ala Lys Leu Arg Lys Met Asn Ser Asp Arg Phe Thr
        490                 495                 500

TAGCAAAACA CCCCATTAGG CATTATTTCA TGTTTTGATT TAGTTTTAGT CCAATATTTG    1594

GCTGATAAGA TAATCCTCCC CGGGAAATCT GAGAGGTCTA TCCCAGTCTG GCAAATTCAT    1654

CAGAGGACTC TTCATTGAAG TGTTGTTACT GTGTTGAACA TGAGTTACAA AGGGAGGACA    1714

TCATAAGAAA GCTAATAGTT GGCATGTATT ATCACATCAA GCATGCAATA ATGTGCAAAT    1774

TTTGCATTTA GTTTTCTGGC ATGATTTATA TATGGCATAT TTATATTGAA TATTCTGGAA    1834

AAATATATAA ATATATATTT GAAGTGGAGA TATTCTCCCC ATAATTTCTA ATATATGTAT    1894

TAAGCCAAAC ATGAGTGGAT AGCTTTCAGG GCACTAAAAT AATATACATG CATACATACA    1954

TACATGCATA TGCACAGACA CATACACACA CATACTCATA TATATAAAAC ATACCCATAC    2014

AAACATATAT ATCTAATAAA AATTGTGATG TTTTGTTCAA AAAAAAAAAA AAAAAACTCG    2074

AG                                                                  2076
```

(2) INFORMATION FOR SEQ ID NO: 2:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Ala Leu Arg Arg Lys Phe Gly Asp Asp Tyr Gln Val Val Thr
 1               5                  10                  15

Thr Ser Ser Ser Gly Ser Gly Leu Gln Pro Gln Gly Pro Gly Gln Gly
            20                  25                  30

Pro Gln Gln Gln Leu Val Pro Lys Lys Arg Gln Arg Phe Val Asp
            35                  40                  45

Lys Asn Gly Arg Cys Asn Val Gln His Gly Asn Leu Gly Ser Glu Thr
 50                  55                  60

Ser Arg Tyr Leu Ser Asp Leu Phe Thr Thr Leu Val Asp Leu Lys Trp
 65                  70                  75                  80

Arg Trp Asn Leu Phe Ile Phe Ile Leu Thr Tyr Thr Val Ala Trp Leu
                85                  90                  95

Phe Met Ala Ser Met Trp Trp Val Ile Ala Tyr Thr Arg Gly Asp Leu
                100                 105                 110

Asn Lys Ala His Val Gly Asn Tyr Thr Pro Cys Val Ala Asn Val Tyr
            115                 120                 125

Asn Phe Pro Ser Ala Phe Leu Phe Phe Ile Glu Thr Glu Ala Thr Ile
 130                 135                 140

Gly Tyr Gly Tyr Arg Tyr Ile Thr Asp Lys Cys Pro Glu Gly Ile Ile
145                 150                 155                 160

Leu Phe Leu Phe Gln Ser Ile Leu Gly Ser Ile Val Asp Ala Phe Leu
                165                 170                 175

Ile Gly Cys Met Phe Ile Lys Met Ser Gln Pro Lys Lys Arg Ala Glu
                180                 185                 190

Thr Leu Met Phe Ser Glu His Ala Val Ile Ser Met Arg Asp Gly Lys
                195                 200                 205

Leu Thr Leu Met Phe Arg Val Gly Asn Leu Arg Asn Ser His Met Val
 210                 215                 220

Ser Ala Gln Ile Arg Cys Lys Leu Leu Lys Ser Arg Gln Thr Pro Glu
225                 230                 235                 240

Gly Glu Phe Leu Pro Leu Asp Gln Leu Glu Leu Asp Val Gly Phe Ser
                245                 250                 255

Thr Gly Ala Asp Gln Leu Phe Leu Val Ser Pro Leu Thr Ile Cys His
                260                 265                 270

Val Ile Asp Ala Lys Ser Pro Phe Tyr Asp Leu Ser Gln Arg Ser Met
                275                 280                 285

Gln Thr Glu Gln Phe Glu Val Val Ile Leu Glu Gly Ile Val Glu
                290                 295                 300

Thr Thr Gly Met Thr Cys Gln Ala Arg Thr Ser Tyr Thr Glu Asp Glu
305                 310                 315                 320

Val Leu Trp Gly His Arg Phe Phe Pro Val Ile Ser Leu Glu Glu Gly
                325                 330                 335

Phe Phe Lys Val Asp Tyr Ser Gln Phe His Ala Thr Phe Glu Val Pro
                340                 345                 350

Thr Pro Pro Tyr Ser Val Lys Glu Gln Glu Glu Met Leu Leu Met Ser
                355                 360                 365
```

-continued

```
Ser Pro Leu Ile Ala Pro Ala Ile Thr Asn Ser Lys Glu Arg His Asn
    370             375             380
Ser Val Glu Cys Leu Asp Gly Leu Asp Asp Ile Ser Thr Lys Leu Pro
385             390             395                         400
Ser Lys Leu Gln Lys Ile Thr Gly Arg Glu Asp Phe Pro Lys Lys Leu
            405             410                     415
Leu Arg Met Ser Ser Thr Thr Ser Glu Lys Ala Tyr Ser Leu Gly Asp
            420             425             430
Leu Pro Met Lys Leu Gln Arg Ile Ser Ser Val Pro Gly Asn Ser Glu
        435             440             445
Glu Lys Leu Val Ser Lys Thr Thr Lys Met Leu Ser Asp Pro Met Ser
    450             455             460
Gln Ser Val Ala Asp Leu Pro Pro Lys Leu Gln Lys Met Ala Gly Gly
465             470             475                         480
Pro Thr Arg Met Glu Gly Asn Leu Pro Ala Lys Leu Arg Lys Met Asn
            485             490             495
Ser Asp Arg Phe Thr
            500
```